United States Patent [19]

Kayser et al.

[11] Patent Number: 4,630,796
[45] Date of Patent: Dec. 23, 1986

[54] X-RAY APPARATUS COMPRISING A PART MOBILE THEREON

[75] Inventors: Harald Kayser, Wedel; Walter Schmedemann, Tangstedt, both of Fed. Rep. of Germany

[73] Assignee: U.S. Philips Corporation, New York, N.Y.

[21] Appl. No.: 725,881

[22] Filed: Apr. 22, 1985

[30] Foreign Application Priority Data

Apr. 30, 1984 [DE] Fed. Rep. of Germany ....... 3416000

[51] Int. Cl.⁴ .............................................. F16M 3/00
[52] U.S. Cl. ................................... 248/648; 248/364; 248/631; 378/193
[58] Field of Search ............ 248/648, 646, 637, 123.1, 248/631, 162.1, 364, 325, 280.1, DIG. 13; 378/193, 194, 197

[56] References Cited

U.S. PATENT DOCUMENTS

| 2,866,101 | 12/1958 | Wagner et al. | 248/280.1 X |
| 3,644,735 | 2/1972 | Vandervelden | 378/197 X |
| 3,933,251 | 1/1976 | Schmedemann | 378/181 |
| 4,166,602 | 9/1979 | Nilsen et al. | 248/123.1 X |
| 4,241,891 | 12/1980 | Rudolph | 248/325 X |
| 4,515,333 | 5/1985 | Pugh et al. | 248/123.1 X |

FOREIGN PATENT DOCUMENTS 0110786 6/1984 European Pat. Off. .
1728886 7/1956 Fed. Rep. of Germany .

Primary Examiner—Ramon O. Ramirez
Attorney, Agent, or Firm—Marc D. Schechter

[57] ABSTRACT

An X-ray apparatus having a hydraulically controlled counterweight. A flexible roll diaphragm seals each piston to each cylinder in the system.

10 Claims, 6 Drawing Figures

X-RAY APPARATUS COMPRISING A PART MOBILE THEREON

BACKGROUND OF THE INVENTION

The invention relates to an X-ray apparatus. The apparatus comprises a part which is movable thereon and a counterweight hydraulically coupled with the moveable part. The counterweight is movable opposite the moveable part. A cylinder system is provided for hydraulically transferring forces.

Such an X-ray apparatus is described in German Pat. No. 1,728,886. In this apparatus, the counterweight is connected to a piston and the moveable part (an X-ray sighting mechanism) is connected with a cylinder. The piston divides the cylinder into two chambers connected through ducts with a fluid pump or the like so that fluid can be pumped from one chamber into the other. As a result, the piston is displaced in the cylinder, and hence the X-ray sighting mechanism is also displaced.

In the rest position (i.e. when no force is exerted on the piston, the X-ray sighting mechanism is held in place by the counterweight. When a force is exerted on the sighting mechanism, the counterweight and the sighting mechanism first move in opposite directions so that only inertia and friction need be overcome. However, as soon as the counterweight has moved over a given distance, the pump is operated so that the X-ray sighting mechanism is displaced by the pump pressure. Since after this operation the counterweight is returned to its initial position, the effort for lifting the X-ray sighting mechanism must be performed by the pump. If the pump or the pump control is defective displacement of the X-ray sighting mechanism is practically impossible.

Another X-ray apparatus is known in which the moveable part can be manually moved by the user German Pat. No. 2,324,699, and U.S. Pat. No. 3,933,251, corresponding thereto.) The part can be moved manually because the counterweight is automatically moved in a sense opposite the X-ray sighting mechanism. The forces are transferred by ropes passed around a number of rollers. The forces required to overcome the friction in the ropes may, when the moveable part is heavy, however, attain unexpectedly high values.

SUMMARY OF THE INVENTION

It is an object of the present invention to provide an X-ray apparatus the moveable part can be displaced by hand without a pump.

According to the invention, both the moveable apparatus part and the counterweight have associated with them a cylinder and a piston. One part of each piston/cylinder pair is fixed and the other part is connected to the moveable apparatus part and to the counterweight, respectively. The fluid space (chamber) enclosed by one piston and cylinder is connected through a hydraulic duct with the corresponding fluid space enclosed by the other cylinder and piston.

According to the invention the moveable apparatus part is, therefore, coupled to one of the cylinders or to one of the pistons. The same applies to the counterweight. When the apparatus part is moved, the volume of the chamber enclosed by the associated cylinder and the associated piston changes. This change in volume produces an equal but opposite change in the volume of the chamber enclosed by the other cylinder and piston. If, for example, the chamber in one system becomes larger, chamber becomes smaller in the other system. By these opposite variations of the volumes of the chambers enclosed by the cylinders and the pistons, opposite movements of the apparatus part and the counterweight can be obtained.

The term "piston" should be construed broadly with regard to this invention. It is not necessary for the piston to divide the cylinder into two chambers as in the known device; in fact the piston may be a tube. It is essential only that the piston and cylinder together should completely enclose a fluid volume with the exception of the opening therein for the hydraulic communication between the two systems of cylinders and pistons.

Since the pistons and the cylinders should be easily movable with respect to each other, and since, on the other hand, they must firmly close the fluid volume, an appropriate seal is required. An extremely accurate matching of the diameters to one another could, indeed, provide a readily displaceable seal. However, the manufacture of such a seal is expensive, and the assembly would be sensitive to even fine granular impurities. Moreover minor leakage of fluid would be unavoidable. Such leakage can, as is known, be avoided almost completely even with less accurate matching of the diameters by interposing elastic sealing rings or sealing sleeves between the piston and the cylinder. However, the sealing rings produce friction, which is the sealing rings too high for the present purpose (about 6 to 10% of the effective force for each cylinder).

In a further aspect of the invention, these disadvantages can be avoided in that the outer diameter of each of the two pistons is markedly smaller than the inner diameter of each cylinder. The intermediate space between the piston and the cylinder is closed by a roll diaphragm which is in tension.

In the use of roll diaphragms the outer edge of the diaphragm is clamped to the cylinder. The diaphragm is squeezed between the piston and cylinder to form a seal. The diaphragm then rolls along the piston wall as the piston is displaced. Since the diaphragm is attached to the cylinder, the maximum piston stroke is limited by the height of the diaphgram.

This limitation can be relaxed when the diaphragm is a tube, the threads of which extend substantially axially or at an acute angle to the axis. Then the elasticity in the circumferential direction is considerably greater than in the longitudinal direction. When subjected to pressure by a fluid medium, such a diaphragm will engage the piston and the cylinder without deflecting in the longitudinal direction. With relative displacement of the piston and the cylinder, the pressure prevents the diaphragm from forming transverse folds hindering the movement.

The tensioning of the diaphragm could be produced by the pressure of the fluid serving for transferring the forces. Then, the fluid should be permanently subjected to pressure. However, in an X-ray examination apparatus pivotable about a horizontal axis, the fluid is not pressurized when the X-ray examination apparatus is horizontal. In this case, the roll diaphragms can be tensioned, for example, by a spring system for supplying biasing forces to the X-ray sighting mechanism and to the counterweight.

Instead, in a further, preferred aspect of the invention, the roll diaphragm is a double diaphragm filled with a liquid or gaseous medium. The pressure of the fluid inside the diaphragm exceeds the pressure of the external fluid for transferring forces. In this case, the bias tension of the roll diaphragm is produced by the higher pressure of the medium contained therein.

In general, the roll diaphragm preferably contains a liquid medium over a gaseous medium because diffusion losses are lower. Also, in the use of a gas, a constant pressure (i.e. a constant tension of the roll diaphragm) cannot be maintained under all conditions. Heating of the gas in the roll diaphragm could give rise to an increase in pressure due to the thermal expansion coefficient. Accordingly, in a further aspect of the invention this problem can be avoided by coupling the inside of the diaphragm with a reservoir containing pressurized gas.

The forces to be exerted by the user in the X-ray apparatus according to the invention depend on the difference between the pressures in the roll diaphragm and in the fluid transferring forces. The higher the difference, the greater are the forces which need to be exerted by the user to displace the X-ray mechanism. Since in an X-ray examination apparatus pivotal about a horizontal axis the pressure of the force transferring fluid depends on the inclination of the X-ray examination apparatus, the pressure difference and the force to be exerted by the user depend (with a constant reservoir pressure) on the inclination.

In a further aspect of the invention, this dependence can be avoided. A container is divided by a diaphragm into two cells. One cell communicates with the force transferring fluid, and the other cell is in contact with the medium inside the roll diaphragm. Means for exerting an additional force on the diaphragm are provided so that the pressure of the medium in the roll diaphragm is higher than the pressure of the force transferring fluid. In this embodiment, the pressure difference is produced only by the additional force on the diaphragm. This additional force may be produced, for example, by a spring. By suitably proportioning this force, the effort of the user for displacing the X-ray mechanism can be particularly slight. In order to limit the length of the counterweight cylinder/piston system while ensuring a sufficient displacement for the apparatus part, the apparatus part and/or the counterweight are connected with the associated cylinder/piston system through a lever. The lever is designed so that in a displacement of the apparatus part or of the counterweight, the cylinder/piston system coupled therewith is displaced to a lesser extent.

SUMMARY OF THE INVENTION

Figure 2C:
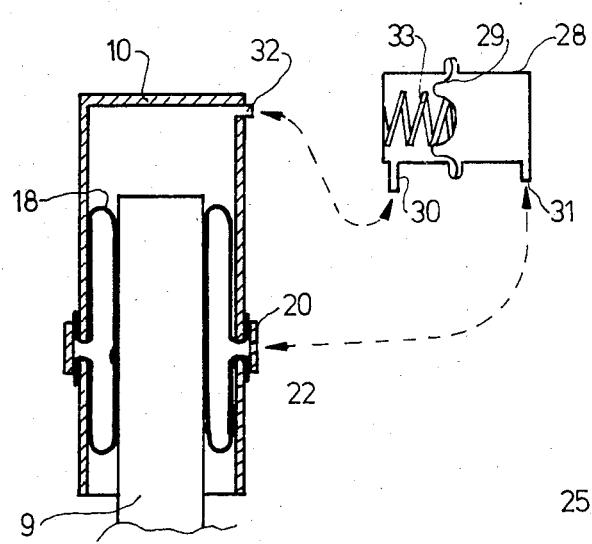
FIG. 2a is a sectional view of a cylinder/piston system according to the invention.
Figure 2B:
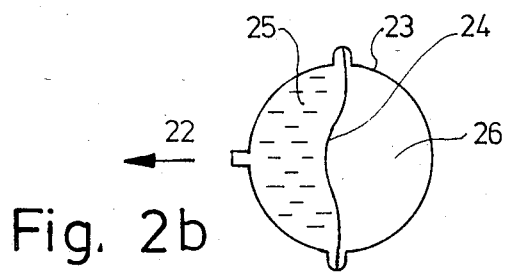

FIG. 2b schematically shows means for producing a constant pressure in the roll diaphragm.

FIG. 2c schematically shows means for producing a constant pressure difference between the pressure inside the roll diaphragm and the pressure in each cylinder.

Figure 3:
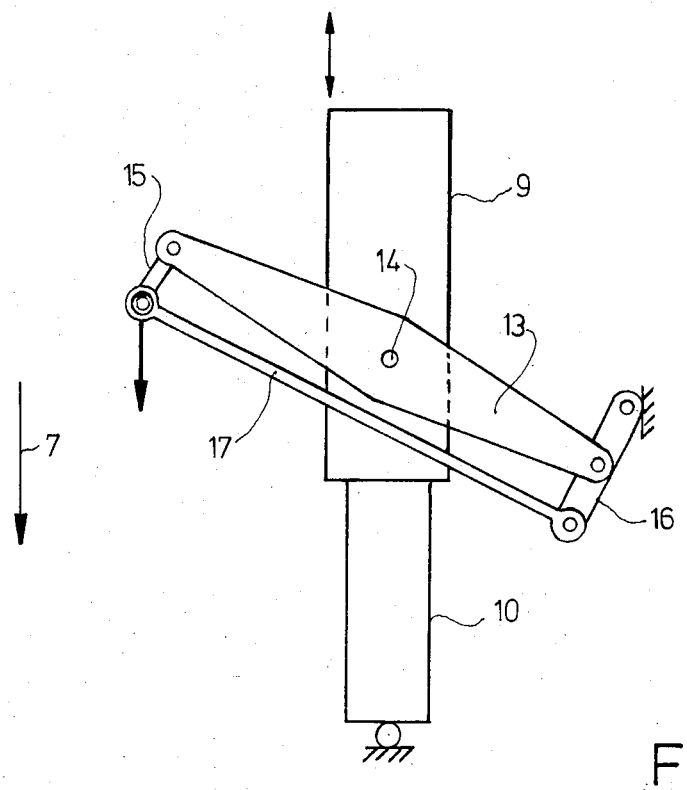

FIG. 3 schematically shows a parallelogram linkage for reducing the required displacement of the counterweight cylinder.

Figure 1:
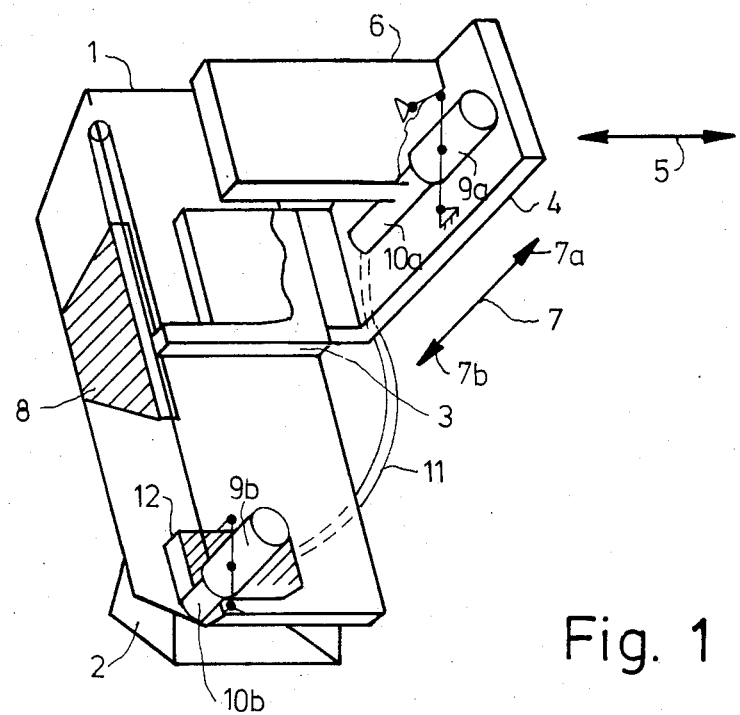
FIG. 1 is a perspective view, partly cut away, of an X-ray examination apparatus according to the invention.
Figure 4:
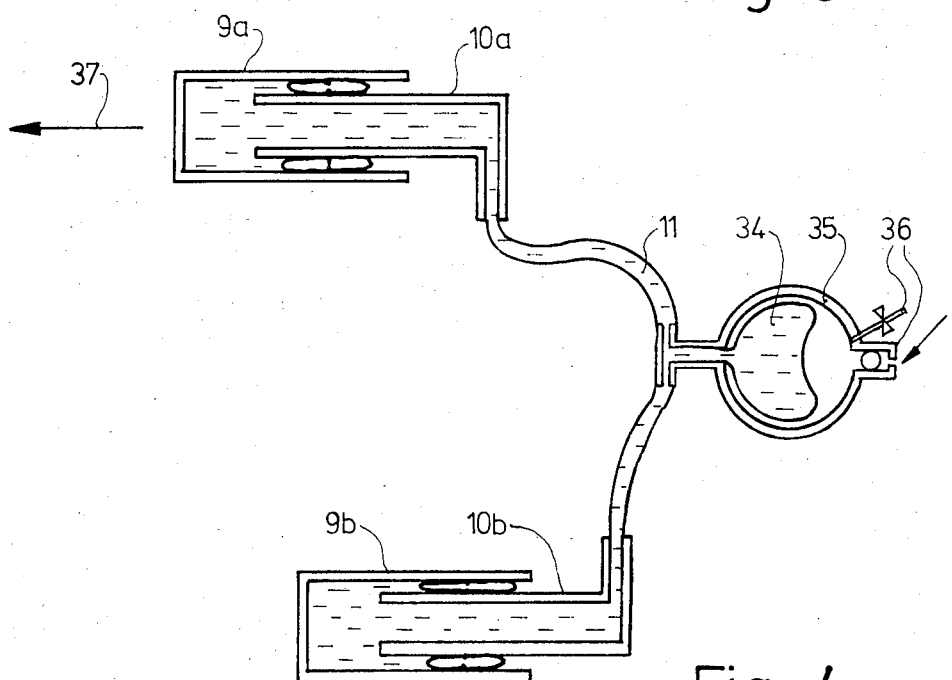

FIG. 4 schematically shows a further embodiment of the apparatus of FIG. 1.

DESCRIPTION OF THE PREFERRED EMBODIMENT

Referring to FIG. 1, a framework 1 of an X-ray examination apparatus is pivotally journalled on a foot 2 about a horizontal axis. A longitudinal carriage 3 is displaceable inside the framework 1 along the length thereof. The longitudinal carriage 3 carries a transverse carriage 4, which is movable on the longitudinal carriage 3 transverse to the length of the apparatus in the direction of the arrow 5. The transverse carriage 4 is provided with an X-ray tube (not shown) and with an X-ray sighting mechanism 6. Mechanism 6 can be moved in the direction of the arrow 7 (i.e. at right angles to the longitudinal and transverse directions) toward or away from a patient.

The weight of the longitudinal carriage 3 with the components carried thereon is compensated for with a main counterweight 8 movable along the length of the framework 1. Counterweight 8 is connected to the longitudinal carriage via ropes passed around rollers.

For compensation of the weight of the X-ray sighting mechanism 6 in the direction of arrow 7, mechanism 6 is coupled to a cylinder 9a. Together with a piston 10a fastened to the transverse carriage 4, cylinder 9a encloses a fluid volume. Likewise at the foot of the frame 1 a compression counterweight 12 is coupled to a cylinder 9b. Together with a piston 10b, cylinder 9b encloses a fluid volume. The fluid volume chamber of cylinder 9b and piston 10b communicates through a hydraulic duct (hose 11) with the fluid volume chamber in the piston 10a and the cylinder 9a.

When the sighting mechanism 6 is moved toward the framework 1, the cylinder 9a moves down and the fluid volume thus displaced lifts the cylinder 9b with the counterweight 12 coupled thereto. The product of the weight 12 and the displacement thereof is equal to the product of the weight of the sighting mechanism 6 and the displacement of the latter. Thus, the mechanism 6 and the weight 12 are in balance. The X-ray sighting mechanism 6 is maintained in its respective position by the counterweight 12, and the X-ray sighting mechanism 6 can be displaced by the user by overcoming only inertia and friction.

From FIG. 1 it is apparent that the sighting mechanism 6 and the counterweight 12 are not directly coupled with the associated cylinders 9a and 9b respectively. Instead they are coupled through lever systems each formed by a parallelogram of rods gripping around the cylinder 10 on two sides. One parallelogram of rods is shown in detail in FIG. 3.

The parallelogram of rods comprises a lever 13, the middle 14 of which is pivotably connected to the cylinder 9. One end of lever 13 is pivotably connected to the end of a rod 15, and the other end of lever 13 is pivotably connected to the middle of rod 16. A rod 17, the length of which is equal to that of the lever 13, is pivotably connected at one end to rod 15 and at the other end to one end of the rod 16, so that the lever 13 and the rods 15, 16 and 17 constitute a parallelogram. The free end of the rod 16 is pivotably connected at a fixed point 40 to the transverse carriage 4 in the framework 1 in a manner such that the point 40, the point 14, and the pivotal joint 42 between the rods 15 and 17 are located in the same plane. The load is fastened at the pivotal joint 42 between the rods 15 and 17. The load is the sighting mechanism 6 or the counterweight 12.

The parallelogram of rods allows the displacement of the cylinder 9 to be half the displacement of the load. Therefore, the length of the cylinder 9 and piston 10 can be small. Also, with the described parallelogram of rods construction, the pivotal points 14 and 42 always move along parallel (in FIG. 3 vertical) straight lines extending in the direction of arrow 7.

Figure 2A:
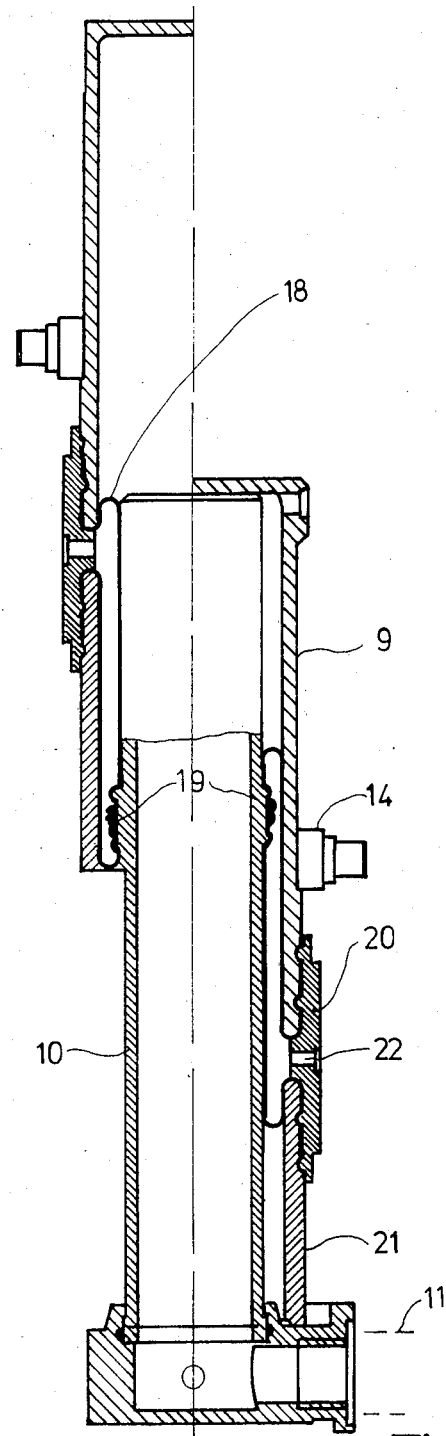

The structure of the piston/cylinder system according to the invention is shown in detail in FIG. 2a. The system is shown in the completely compressed state on the right-hand side of the center line, and is shown in the fully extended state on the left-hand side of the center line.

The piston 10 is a tube having at its lower end a connection for the hose 11 (FIG. 1). The cylinder 9 surrounding the piston 10 is closed at the top end by a head face. The inner diameter (for example 62 mm) of the cylinder 9 is markedly larger than the outer diameter of the piston 10 (for example 46 mm) so that there is a relatively large space between piston 10 and cylinder 9.

The space between cylinder 9 and piston 10 is sealed with a bilateral roll diaphragm 18 which surrounds the piston 10. The middle of the roll diaphragm 18 is in contact with the whole periphery of the piston 10 at area 19. The ends of roll diaphragm 18 are connected by a pressure ring 20 to the lower end of the cylinder 9 and to a cylinder part 21 which functions only as a guide element. The inner and outer diameters of guide 21 correspond with those of the cylinder 9. The bilateral roll diaphragm 18 thus seals the space between the cylinder 9 and the piston 10 and retains a preferably liquid medium, for example glycerine inside the roll diaphragm.

The pressure of the fluid inside the roll diaphragm exceeds the pressure of the force transferring fluid (which is bounded by the cylinder 9, one side of the roll diaphragm 18 and the piston 10). Therefore, the roll diaphragm bows out and rolls without folds along the inner surface of the cylinder and along the outer surface of the piston when the piston is displaced. Due to the pressure in the interior of the roll diaphragm, the cylinder 9 is oriented coaxially with respect to the piston 10.

If the pressure inside the roll diaphragm were lower than the pressure of the force transferring fluid, the roll diaphragm would form sharp folds on the side facing the pistons and cylinder. Such folds would practically block displacement between the piston and cylinder.

The elasticity of the roll diaphragm should be as small as possible at least in the axial direction. The roll diaphragm can consist of a sheet of axially extending yarn sealed on both sides by a rubber skin. The thinner the roll diaphragm, the lower are the energy losses in the diaphgram when the cylinder is displaced and the lower are the forces to be exerted by the user for moving the sighting mechanism. The energy losses are, however, also determined by the diameters of the inner surface of the cylinder and the outer surface of the piston. The greater is the difference in diameters, the greater is the diameter of the fold of the roll diaphragm, and the lower are the losses. On the other hand, the load on the diaphragm increases with the magnitude of the annular space between the piston and cylinder, so that greater differences in diameters, may require thicker roll diaphragms.

As stated above, the inner pressure in the roll diaphragm must exceed the pressure of the force transferring fluid. This higher inner pressure can be maintained by hermetically closing the interior of the roll diaphragm. Due to thermal expansion and to the slight elasticity of the roll diaphragm, however, slight pressure fluctuations might occur. These pressure fluctuations can be avoided when the interior of the roll diaphragm is connected through an opening 22 in the pressure ring 20 with a pressure reservoir. This pressure reservoir is schematically shown in FIG. 2b. It is a metal vessel 23, which is divided by an elastic diaphragm 24 into two chambers. The chamber 25 is filled with the fluid also contained in the roll diaphragm and communicates therewith through the outlet 22. The second chamber 26 is hermetically closed to the outside and contains a pressurized gas, for example nitrogen.

The energy losses also increase as the pressure differences between the fluid in the roll diaphragm and (i) the atmospheric pressure and (ii) the pressure of the force transferring fluid increase. The highest losses, therefore, occur in the embodiment having constant pressure in the roll diaphragm when the table of the X-ray examination apparatus is perpendicular because in this case the pressure of the force transferring fluid is practically zero so that the pressure difference is high.

This disadvantage can be avoided when the reservoir 23 provides only the pressure difference required for maintaining the minimum tension in the roll diaphragm. Such a reservoir is shown in FIG. 2c and comprises a vessel 28. Vessel 28 is again divided by a diaphragm 29 into two compartments, each of which has an outlet 30 and 31, respectively. The outlet 31 is connected to the opening 22 in pressure ring 20. The outlet 30 is connected to an opening 32 near the head face of the cylinder 9 through a hose (not shown). The chamber in vessel 28 which is connected to the outlet 32 is provided with a compression spring 33. Spring 33 exerts pressure on part of the surface of diaphragm 29. Without the spring, the diaphragm 29 would move to equalize the pressures in the interior of the roll diaphragm and of the force transferring fluid. Due to the spring 33, however, the pressure in the chamber provided with the outlet 31 is raised so that the pressure in the roll diaphragm is higher by a predetermined, spring-dependent value than the pressure of the force transferring fluid.

In the event the roll diaphragm develops a leak, the diaphragm 29 would be displaced to the right by the spring force. When a suitable switch is arranged at this place, for example a reed contact actuated by a magnet, an alarm signal can be produced when the diaphragm is displaced too far.

As stated above, the pressure of the force transferring fluid disappears when the X-ray examination apparatus is turned into its perpendicular position. When in this position the X-ray sighting mechanism is moved by a slight force, the counterweight can follow the movement. However, if the force exerted on the sighting mechanism exceeds a critical value corresponding to the product of the atmospheric pressure and the active piston surface, a vacuum or a sub-atmospheric pressure occurs so that vapor is formed in the fluid. Then, the counterweight does not move as rapidly as the sighting mechanism and produces a disturbing audible impact at the collapse of the vapor bubble.

The desired function of the counterweight is only to support the X-ray sighting mechanism 6 in the direction 7a (upward). Thus, when the table 1 is perpendicular, it is advantageous to decouple the counterweight 12 from the X-ray device 6. This decoupling is shown in FIG. 4. The hose 11 communicates with an elastic bladder 34 in the interior of a rigid housing 35. Housing 35 is provided with an opening or a valve system 36 so that air can flow into and out of the housing. The air flow may, if desired, be damped. When a force is exerted in the direction of the arrow 37 or 7a, (i.e. a tensile force) on the sighting mechanism 6 or the cylinder 9a connected therewith, the increasing volume in the system 9a, 10a is filled by the fluid flowing out of the elastic bladder 34. The cylinder 9b does not shift with respect to the cylinder 10b, which means that the counterweight 12 is no longer coupled to the movement of the sighting mechanism. This has the advantage that the user only has to move the mass of the sighting mechanism.

When the X-ray examination apparatus is turned out of the perpendicular position, the valve 36 is closed and the fluid is again pressurized. A small choke is opened so that the elastic bladder 34 expands and expells the occluded air slowly until the elastic bladder 34 abuts the entire inner wall of the housing 35. Thus, coupling between the sighting mechanism and the counterweight is established smoothly rather than with a shock. Then, the movements of the cylinders 9a and 9b are again coupled with one another.

It is not absolutely necessary for the two cylinder/piston systems connected to the sighting device 6 and the counterweight 12, respectively, to have identical dimensions. If they have different dimensions, different transmission ratios can be obtained (which means that the cylinders are not shifted over the same distances). This may be utilized to obtain weight compensation with smaller counterweights or smaller lifts of the cylinders.

It is not important for the cylinder to enclose the piston. Indeed the cylinder could be arranged in the interior of the tubular piston and could be connected to the piston through a roll diaphragm.

In order to reduce the length of the structure, two pistons of preferably different diameters could be moved into a cylinder from opposite directions so that they penetrate one into the other. The pistons must then be closed on both sides, and the cylinder diameter must be adapted in an axial direction so the space between the cylinder inner wall and each piston outer wall is at the same distance from the axis of the cylinder. Alternatively, telescoping pistons can be used.

What is claimed is:

1. An X-ray apparatus comprising:
   a frame;
   a first part moveable with respect to the frame;
   a first piston/cylinder assembly having a chamber between the piston and the cylinder, said chamber being filled with a volume of fluid, said first assembly having one of the piston or cylinder attached to the frame and the other attached to the first part;
   a counterweight moveable with respect to the frame;
   a second piston/cylinder assembly having a chamber between the piston and the cylinder, said chamber being filled with a volume of fluid, said second assembly having one of the piston or cylinder attached to the frame and the other attached to the counterweight; and
   a hydraulic duct for providing fluid communication between the chamber in the first piston/cylinder assembly and the chamber in the second piston/cylinder assembly;
   whereby movement of the first part in a first direction relative to the frame changes the volume of fluid in the chamber of the first piston/cylinder assembly, the change in the volume of fluid in the chamber of the first piston/cylinder assembly produces an equal but opposite change in the volume of fluid in the chamber of the second piston/cylinder assembly, and the change in the volume of fluid in the chamber of the second piston/cylinder assembly causes movement of the counterweight in a second direction opposite to the first direction.

2. An X-ray apparatus as claimed in claim 1, characterized in that:
   in each piston/cylinder assembly, the piston has a side wall with an outside diameter and the cylinder has a side wall with an inside diameter which is greater than the outside diameter of the side wall the piston to form a space between the side walls; and
   each piston/cylinder assembly has a roll diaphragm arranged between the piston and cylinder side walls to seal the space therebetween, said roll diaphragm being in tension.

3. An X-ray apparatus as claimed in claim 2, characterized in that the roll diaphragm has a hydraulic medium therein at a pressure greater than the pressure outside the roll diaphragm.

4. An X-ray apparatus as claimed in claim 3, characterized in that the hydraulic medium in the roll diaphragm is coupled to a first chamber of a pressure reservoir, said pressure reservoir having a second chamber containing pressurized gas, the first and second reservoir chambers being separated by a diaphragm.

5. An X-ray apparatus as claimed in claim 3, characterized in that the apparatus further comprises a pressure regulator having first and second chambers separated by a diaphragm, said first regulator chamber having means for pressing the diaphragm into the second regulator chamber, said first regulator chamber being hydraulically coupled to the piston/cylinder chambers, said second regulator chamber being hydraulically coupled to the hydraulic medium in the roll diaphragm.

6. An X-ray apparatus as claimed in claim 3, characterized in that the piston/cylinder chambers are hydraulically coupled to a variable volume container.

7. An X-ray apparatus as claimed in claim 6, characterized in that the variable volume container comprises an elastic bladder in a rigid housing, the housing having a controllable opening therein.

8. An X-ray apparatus as claimed in claim 7, characterized in that the controllable opening comprises a valve with damping.

9. An X-ray apparatus as claimed in claim 3, characterized in that the apparatus further comprises an arrangement of levers for coupling the first part to its piston/cylinder assembly.

10. An X-ray apparatus as claimed in claim 3, characterized in that the apparatus further comprises an arrangement of levers for coupling the counterweight to its piston/cylinder assembly.

* * * * *